(12) United States Patent
Steele et al.

(10) Patent No.: US 9,327,893 B2
(45) Date of Patent: May 3, 2016

(54) SANITARY FITTING WITH PARABOLIC ENTRANCE AND VORTEX-FORMING, SUCTION-RELIEF RIBS

(75) Inventors: Kyle R. Steele, Fort Collins, CO (US); Carl T. Whitaker, Berthoud, CO (US); Ravikumar Narayanan, Fort Collins, CO (US); Douglas Kimmel, Fort Collins, CO (US)

(73) Assignee: Nordson Corporation, Westlake, OH (US)

( * ) Notice: Subject to any disclaimer, the term of this patent is extended or adjusted under 35 U.S.C. 154(b) by 0 days.

(21) Appl. No.: 13/414,685

(22) Filed: Mar. 7, 2012

(65) Prior Publication Data
US 2012/0228873 A1    Sep. 13, 2012

Related U.S. Application Data

(60) Provisional application No. 61/450,083, filed on Mar. 7, 2011.

(51) Int. Cl.
*F16L 33/00*    (2006.01)
*B65D 75/58*    (2006.01)

(52) U.S. Cl.
CPC ........ *B65D 75/5877* (2013.01); *A61M 2206/14* (2013.01)

(58) Field of Classification Search
USPC ............... 285/59, 60, 399, 239; 137/808, 809
See application file for complete search history.

(56) References Cited

U.S. PATENT DOCUMENTS

| | | | | |
|---|---|---|---|---|
| 1,312,152 | A | * | 8/1919 | Barrow ..................... 285/288.2 |
| 3,481,632 | A | * | 12/1969 | Suess .................. E04D 13/0409 |
| | | | | 285/136.1 |
| 3,642,018 | A | * | 2/1972 | Egolf et al. ................... 137/808 |
| D252,703 | S | | 8/1979 | Cupit |
| 4,581,142 | A | * | 4/1986 | Fladby et al. .............. 210/512.1 |
| D287,872 | S | | 1/1987 | Eriksson |
| D318,101 | S | | 7/1991 | Rodgers |
| 5,070,972 | A | | 12/1991 | Dourson et al. |
| 5,188,868 | A | * | 2/1993 | Horii et al. .................... 427/212 |

(Continued)

FOREIGN PATENT DOCUMENTS

| | | |
|---|---|---|
| DE | 7402178 | 11/1975 |
| DE | 69800752 | 4/2002 |

(Continued)

OTHER PUBLICATIONS

International Search Report and Written Opinion dated May 11, 2012, PCT/US2012/028142, 12 pages.

(Continued)

*Primary Examiner* — Aaron Dunwoody
(74) *Attorney, Agent, or Firm* — Baker & Hostetler LLP

(57) ABSTRACT

A sanitary fitting has a flange portion, a connector portion, and a parabolic entrance disposed therebetween. The flange portion has a planar ring surface that defines a central opening. The connector portion defines a lumen extending from the central opening toward an outlet port. The parabolic entrance surface extends from the planar ring surface and transitions into the connector portion to define a portion of the lumen. One or more suction-relief ribs may be arranged along the surface of the flange portion and extend into the parabolic entrance. The suction-relief ribs may have a twisting curvature for causing rotation of fluid flow through the sanitary fitting.

23 Claims, 9 Drawing Sheets

(56) References Cited

U.S. PATENT DOCUMENTS

| | | | |
|---|---|---|---|
| 5,320,389 A | | 6/1994 | Dupont, Jr. |
| 5,464,039 A | * | 11/1995 | Bergamini .................. 137/551 |
| 5,817,113 A | | 10/1998 | Gifford, III et al. |
| 5,837,180 A | | 11/1998 | Linder et al. |
| 5,971,438 A | | 10/1999 | Johnson |
| D464,409 S | | 10/2002 | Nishio |
| 6,679,529 B2 | | 1/2004 | Johnson et al. |
| 6,696,018 B2 | | 2/2004 | Buchanan |
| 6,764,284 B2 | | 7/2004 | Oehman, Jr. |
| 6,782,333 B2 | | 8/2004 | Baker et al. |
| 6,893,428 B2 | | 5/2005 | Willemstyn |
| 7,284,731 B1 | | 10/2007 | Johnson et al. |
| 7,481,462 B2 | | 1/2009 | Arning et al. |
| 2002/0148857 A1 | | 10/2002 | Savage et al. |
| 2003/0226857 A1 | | 12/2003 | Bibbo et al. |
| 2007/0044487 A1 | * | 3/2007 | Craig .......................... 62/63 |
| 2007/0102450 A1 | | 5/2007 | Stiers |
| 2008/0105313 A1 | | 5/2008 | Gloor et al. |
| 2009/0119886 A1 | | 5/2009 | Werth |
| 2009/0232595 A1 | | 9/2009 | Willemstyn et al. |
| 2010/0133807 A1 | | 6/2010 | Bilstad et al. |
| 2012/0222764 A1 | * | 9/2012 | Hermann et al. ............. 137/808 |

FOREIGN PATENT DOCUMENTS

| | | |
|---|---|---|
| DE | 202009015434 | 5/2010 |
| EP | 0803273 | 10/1997 |
| EP | 0841085 | 5/1998 |
| EP | 2003926 | 12/2008 |
| GB | 2437301 | 10/2007 |
| JP | 2000/170235 | 6/2000 |
| WO | WO 2010/040779 | 4/2010 |

OTHER PUBLICATIONS

Bioeaze San Tri-Clamp 3/8 BRB, http://www.safcglobal.com/etc/medialib/docs/Sigma/Product_Information_Sheet/1807p.PAR.0001.File.tmp/1807p.pdf, known at least as early as Sep. 28, 2010, 1 page.

BioProcessing Fittings, Value Plastics, Inc., http://www.valueplastics.com/products/sanitary_fittings.aspx, known at least as early as Sep. 28, 2010, 3 pages.

Mitos BioSystems, Mitos Technologies, Inc., http://www.mitostech.com/biooptions.html, known at least as early as Sep. 28, 2010, 12 pages.

Port Plate—Media Bag and Bio-reactor Connector Plates, Eldon James Corp., http://www.bioresearchonline.com/product.mvc/Port-Plate-Media-ag-and-Bio-reactor-Connecto-0001?VNETCOOKIE=NO, known at least as early as Sep. 28, 2010, 2 pages.

Rubber Fab Sanitary Tri-Clamp Reusable Hose Fittings, Rubber Fab Item # RF04HB08RTCSS, JME Ellsworth, https://www.jmesanitary.com/Rubber-Fab-Sanitary-Tri-Clamp-Reusable-Hose-Fittings-103528.aspx, known at least as early as Sep. 28, 2010, 2 pages.

Sanitary Fittings, ThermoplasticBioLogic, http://www.thermoplasticbiologic.com/fittings_sanitary.html, known at least as early as Sep. 28, 2010, 3 pages.

* cited by examiner

SANITARY FITTING WITH PARABOLIC ENTRANCE AND VORTEX-FORMING, SUCTION-RELIEF RIBS

CROSS REFERENCE TO RELATED APPLICATION

This application claims the benefit of priority pursuant to 35 U.S.C. §119(e) of U.S. provisional patent application No. 61/450,083 filed 7 Mar. 2011, entitled "Bag Port with Parabolic Lead-In and Vortexing Suction Relief Ribs", the contents of which are hereby incorporated by reference as if fully set forth herein.

TECHNICAL FIELD

The present disclosure relates to sanitary fittings or ports, typically for use with sealed chemical bags in the chemical/biochemical/pharmaceutical manufacturing industries.

BACKGROUND

Sterility is a large concern in certain fields, such as biopharmaceutical manufacturing. Many different chemicals, both dry and in solution, may be used during the manufacturing process. Often such chemicals are provided in hermetically sealed bags. Providing sealable sanitary fittings with ports allowing access to the interior portion of a sealed bag enables a sterile environment within the bag to be maintained while allowing the contents of the bag to be emptied.

Sanitary fittings are typically composed of a connector portion that defines a fluid flow path and provides a structure for attachment to fluid tubing of a connector and a flange portion that is hermetically sealed to the bag. Sanitary fittings may be joined to bags in several ways, most commonly through welding processes. The flange portion used to secure the port to the bag is first mated to the bag, and a heating element or RF welding fixture melts (welds) the bag to the flange. This weld is made to be impermeable, which maintains sterility within the bag. Once the bag is joined to the sanitary fitting, materials can be transferred through the port portion of the sanitary fitting into and out of the bag while maintaining this sterility.

The information included in this Background section of the specification, including any references cited herein and any description or discussion thereof, is included for technical reference purposes only and is not to be regarded subject matter by which the scope of the invention as defined in the claims is to be bound.

SUMMARY

Sanitary fittings are disclosed herein that maintain sterility and allow contents to be drained as quickly as possible by providing sanitary fitting ports with port entrance features and/or geometries that encourage optimal flow of the bag contents.

In one implementation, a sanitary fitting may have a flange portion, a connector portion, and a parabolic entrance disposed therebetween. The flange portion may have a planar ring surface that defines a central opening. The connector portion may define a lumen extending from the central opening toward an outlet port. The parabolic entrance surface extends from the planar ring surface and transitions into the connector portion to define a portion of the lumen.

In another implementation, a sanitary fitting may have a flange portion, a connector portion, a parabolic entrance disposed therebetween, and a suction-relief rib. The flange portion may define a flat face and a central opening therein. The connector portion extends from the flange portion and defines an outlet port. The parabolic entrance to the outlet port may be formed by a continuous sidewall that defines the central opening extending from an inner perimeter edge of the flat face to the outlet port of the connector portion. The suction-relief rib may be arranged along the flat face of the flange portion and extend into the parabolic entrance. The suction-relief rib may have a twisting curvature for causing rotation of fluid flow through the sanitary fitting.

In a further implementation, a sanitary fitting may have a flange portion, a connector portion extending from the flange portion and defining a lumen therethrough, and a plurality of suction-relief ribs positioned on the flange portion around an entrance opening to the lumen and configured to cause a vortex in fluid flow through the lumen.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. A more extensive presentation of features, details, utilities, and advantages of the present invention is provided in the following written description of various embodiments of the invention, illustrated in the accompanying drawings, and defined in the appended claims.

BRIEF DESCRIPTION OF THE DRAWINGS

FIG. 1 is a top isometric view of an implementation of a sanitary fitting with a parabolic lead-in.

FIG. 4 is a top right isometric view of another implementation of a sanitary fitting with a parabolic lead-in.

FIG. 5 is an isometric view of an implementation of a sanitary fitting with vortex-forming, suction-relief ribs and a parabolic lead-in.

FIG. 9 is a top isometric view of another implementation of a sanitary fitting with vortex-forming, suction-relief ribs and a parabolic lead-in.

DETAILED DESCRIPTION

Sanitary fittings as disclosed may be used in the sterile transfer materials. The sanitary fittings may include a parabolic lead-in geometry between a flange portion and a port portion and vortex-forming suction-relief ribs on the flange portion, the connector portion, or both, and each may facilitate optimal material flow through the sanitary fitting. The sanitary fittings may be configured as ports for receptacles such as bags and containers in sterile settings such as in the pharmaceutical industry. In some implementations, the connector portions of the sanitary fittings may be configured as hose barbs, reducers, or as ferrules.

Parabolic Lead-In

Figure 1:
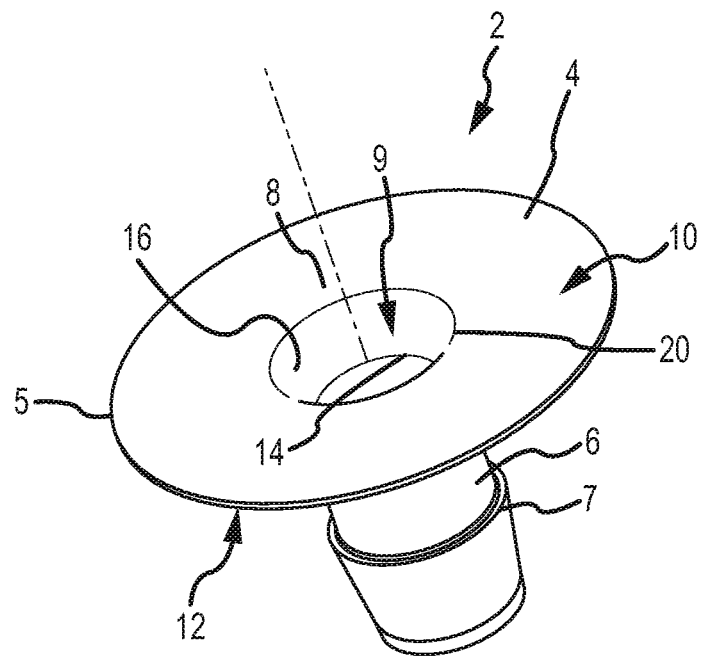
Figure 2:
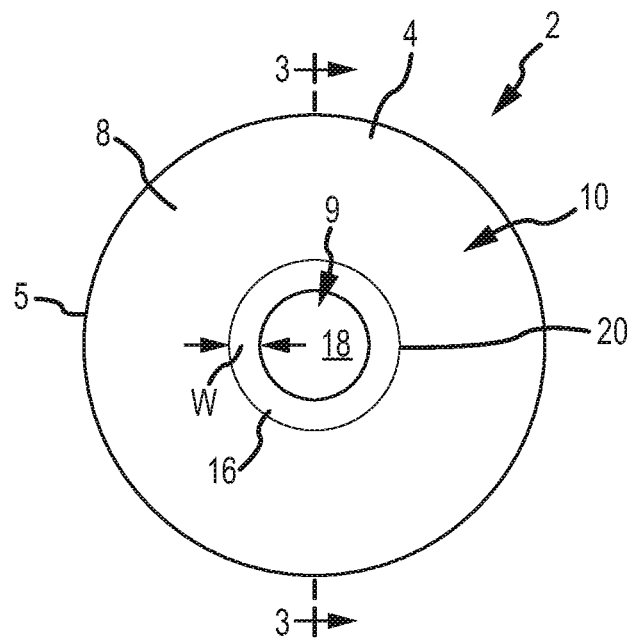
FIG. 2 is a top plan view of the sanitary fitting illustrated in FIG. 1.
Figure 3:
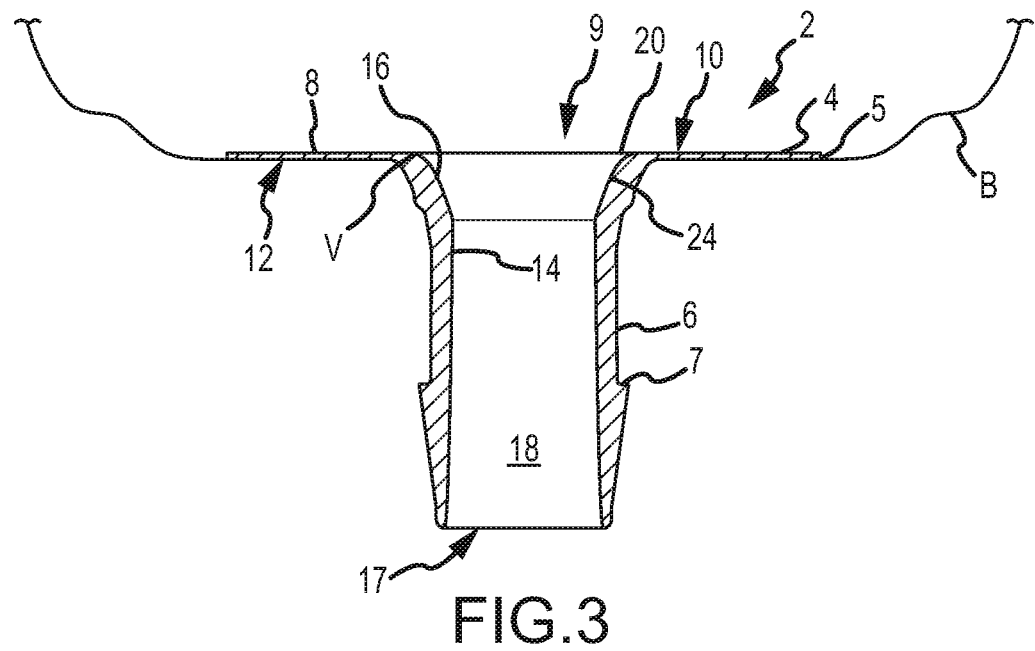
FIG. 3 is a cross-section view of the sanitary fitting of FIG. 1 taken along the line 3-3 as illustrated in FIG. 1.

FIGS. 1-3 depict an implementation of a sanitary fitting 2 that may join to a bag B for the sterile transfer of bag contents. The sanitary fitting 2 may include a flange portion 4 and a connector portion 6.

The flange portion 4 of the sanitary fitting 2 maybe configured as a planar structure with a circular outer circumference 5 and may define planar ring 8 defining a central opening 9 extending through the flange portion 4 from a flat face 10 of the flange portion 4 to a connector mating side 12 of the flange portion 4.

The connector portion 6 of the sanitary fitting 2 may be configured as a cylindrical wall 14 that defines a lumen 18. The connector portion 6 may join or be integrally formed with the flange portion 4 as the connector portion 6 transitions into the connector mating side 12 of the flange. An annular barb 7 may be formed on an outer wall of the connector portion 6. The cylindrical wall 14 of the connector portion 6 may taper and a thickness of the cylindrical wall 14 may decrease as the cylindrical wall 14 of the connector portion 6 terminates at an outlet port 17.

The flange portion 4 and the connector portion 6 of the sanitary fitting 2 may be formed so that both the central opening 9 of the planar ring 8 of the flange portion 4 and the lumen 18 of the connector portion 6 align along a central axis of the sanitary fitting 2. The planar ring 8 of the flange portion 4 may transition to a parabolic entrance 16 formed with a parabolic lead-in geometry. The parabolic entrance 16 may start from a nose 20 (a circular transition line) on the flat face 10 of the flange portion 4 and may extend to transition into the cylindrical wall 14 of the connector portion 6. As discussed below, the parabolic entrance 16 may improve flow characteristics of materials flowing through the sanitary fitting 2. The planar ring 8 of the flange portion 4, the parabolic entrance 16, and the cylindrical wall 14 of the connector portion 6 together may define the lumen 18 to provide continuous flow pathway allowing flow into or out of the sanitary fitting 2.

As shown in FIG. 3, the parabolic entrance 16 of the sanitary fitting 2 may form a parabolic-shaped cross-section 24 that initiates at the nose 20 of the flange portion 4. The nose 20 may be formed at point where the flat face 10 of the flange portion 4 begins to transition to form the parabolic entrance 16. FIG. 2 illustrates a top plan view of the sanitary fitting 2, which shows the flat face 10 and a transition from the flat face 10 at the nose 20 to the parabolic entrance 16. The cross-section 24 of the parabolic entrance 16 may be formed as a parabolic curve having a vertex V located at the nose 20. The ratio of the minimum diameter where the parabolic entrance 16 merges with the cylindrical wall 14, to the maximum diameter of the nose 20 located on the flat face 10 may be described as Dmax=0.7×Dmin+0.125, where Dmax is the diameter of the nose 20 located on the flat face 10, and Dmin is the minimum diameter where the parabolic entrance 16 merges with the cylindrical wall 14. A length of the parabolic entrance 16 may be selected based on the desired width W of the parabolic section (i.e., the distance between the nose 20 and the start of the cylindrical wall when considered from a plan view as shown in FIG. 2) and the diameter of the cylindrical lumen 18 within the cylindrical wall 14. The parabolic entrance 16 may transition outwardly and downwardly as it initially extends from the nose 20 of the flange portion 4. The parabolic entrance 16 may be understood as extending between an outer diameter at the nose 20 and an inner diameter corresponding to the diameter of the lumen 18 defined by the cylindrical wall 14 of the connector portion 6.

The components of the sanitary fitting 2 may be integrally formed, for example, by injection molding and overmolding processes. While the sanitary fitting 2 is depicted with a flange portion 4 having a circular external circumference, the external circumference or perimeter of the flange portion 4 may define any shape or configuration useful for connecting the sanitary fitting to a bag B or other structure for holding contents needing transfer via the sanitary fitting 2, to a conduit. While the sanitary fitting 2 is shown as having a connector portion 6 with a barbed end 7 for connecting with a length of tubing, for example, the connector portion 6 may have any exterior configuration useful for mating with structures that facilitate the transport of the contents from the bag B. Moreover, while the sanitary fitting 2 is shown as defining an axially extending central opening 9 and lumen 18 having cylindrical cross sections, in other embodiments the central opening may comprise an oval shape or another shape useful for transferring contents via sanitary fitting 2.

Figure 4:
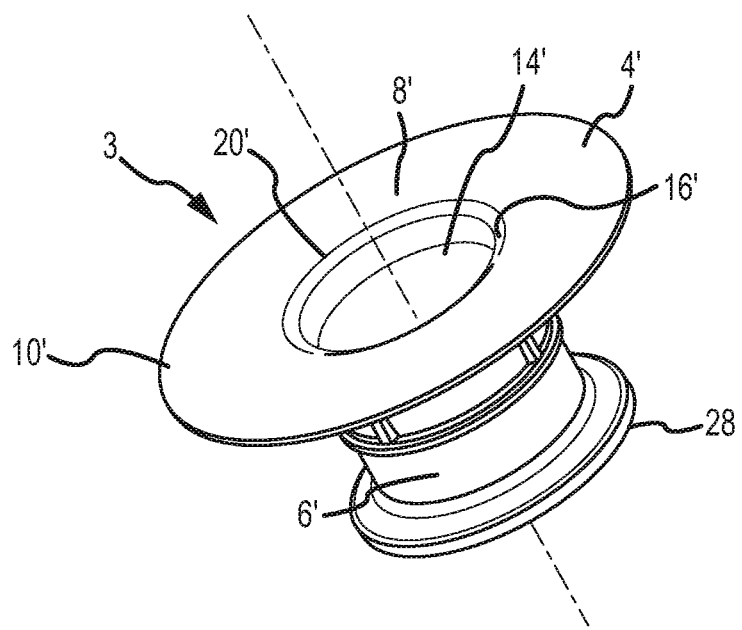
Figure 5:
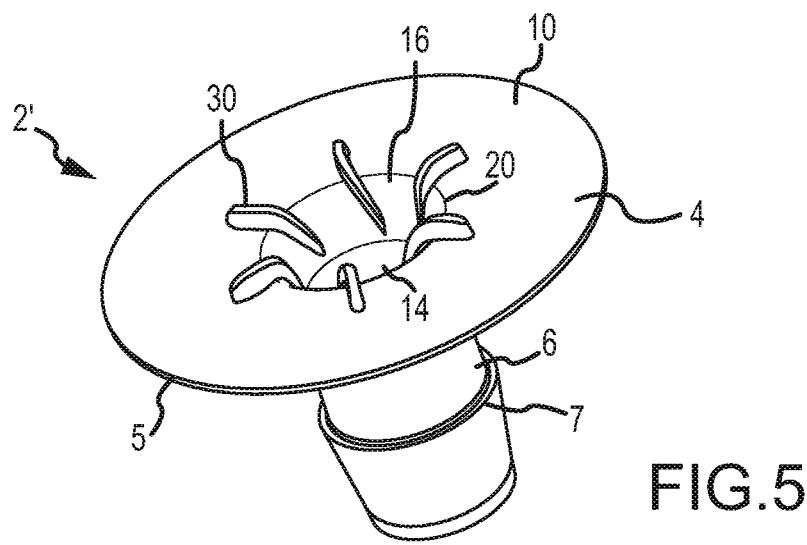

FIG. 4 depicts another implementation of a sanitary fitting 3, with features similar to FIGS. 1-3 numbered similarly. The sanitary fitting 3 differs from the sanitary fitting 2 due to the relatively larger internal diameters of both the planar ring 8' of the flange portion 4' and the cylindrical wall 14' of the connector portion 6'. In addition, the sanitary fitting 3 includes a connector portion 6' with ferrule or clamp flange 28, which may be clamped together with the flange of an opposing connector, e.g., via joining or abutting end faces of the clamp flange 28 of the sanitary fitting 3 with the flange of the opposing connector and engaging a clamp around an external circumference of the flanges. In some implementations, the clamp flange 28 may be connected with another structure such as a cap, tube, valve, bag, vessel, and so on.

Vortex-Forming Suction-Relief Ribs

Figure 8A:
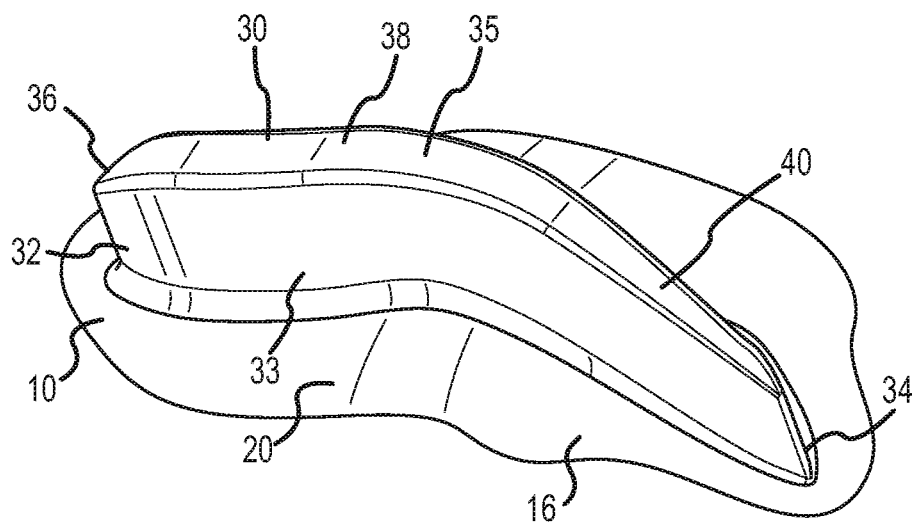
FIG. 8A is an enlarged view of a rib of the sanitary fitting of FIG. 5.
Figure 8B:
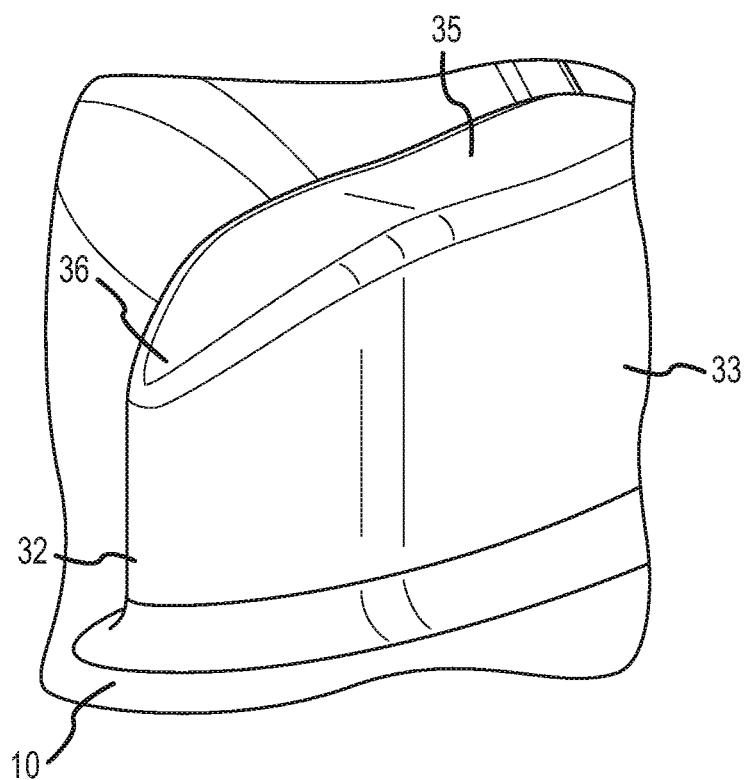
FIG. 8B is another enlarged view of a rib of the sanitary fitting of FIG. 5.
Figure 9:
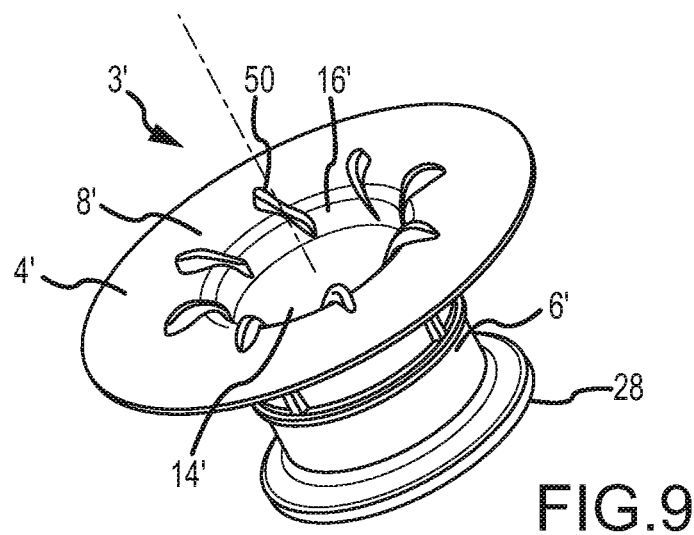

FIGS. 8A and 8B depict another implementation of a sanitary fitting 2 with the addition of vortex-forming suction-relief ribs 30 having a parabolic geometry, where features similar to FIGS. 1-3 are numbered the same. The vortex-forming suction-relief ribs 30 may have a twisting curvature as the suction-relief ribs 30 extend along the flange portion 4 and into the parabolic entrance 16 of the sanitary fitting 2. The suction-relief ribs 30 may protrude generally normally to the flat face 10 of the flange portion 4 and the parabolic entrance 16. As the suction-relief ribs 30 extend from the nose 20 into the parabolic entrance 16, the suction-relief ribs 16 may define a parabolic nose geometry as further described below. At the intersection between the relief ribs 30 and the sanitary fitting 2, the sidewalls of the relief ribs 30 may flare outwardly, as described further below. The vortex-forming suction-relief ribs 30 may be integrally formed with or joined to the sanitary fitting 2'. While six vortex-forming suction-relief ribs 30 are shown in an equally spaced manner around the lumen 18 of the sanitary fitting 2', the sanitary fitting 2' is not limited to this configuration and may be provided with more or less than six ribs 30 with equal or variable or nonuniform spacing.

Figure 6:
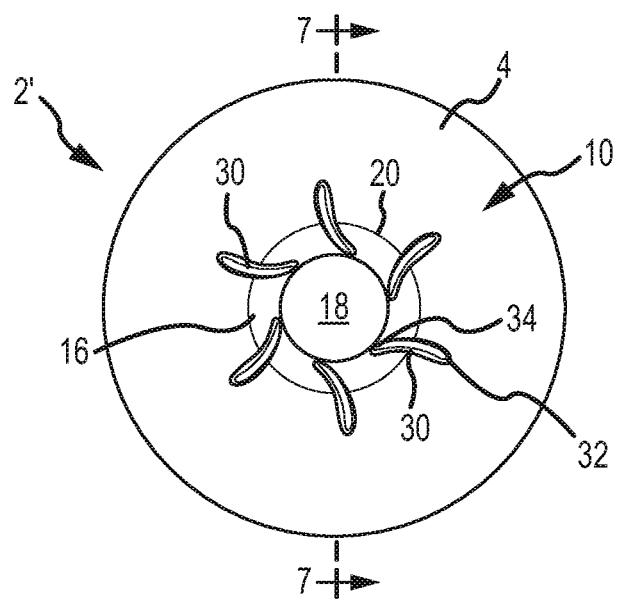
FIG. 6 is a top plan view of the sanitary fitting of FIG. 5.

With reference to FIGS. 5-8B, the shape of the vortex-forming suction-relief ribs 30 may follow the form of an airfoil along a length of the sidewalls of the ribs 30. The airfoil shape may include a parabolic-shaped leading edge 32, which may form a parabola-shaped end that opens in the direction of the central opening 9 of the flange portion 4. (See FIG. 8B). The leading edge 32 of the suction-relief rib 30 may transition to a sidewall 33 on each side of the rib 30. A thickness is defined between the sidewalls 33 that remains substantially constant as the ribs 30 extend towards the central opening 9 along the flat face 10 of the flange portion 4. As the ribs 30 continue into the parabolic entrance 16, the sidewalls 33 may be configured with a twisting curvature and may begin to taper. In FIG. 6, the taper and twist of the ribs 30 initiates substantially at the nose 20 of the flange portion 4. The twisting curvature of the ribs 30 may have an angle of pitch between about 9 and about 12 degrees, between about 10 and about 15 degrees, between about 10 and 20 degrees, or less than 30 degrees. The tapering sidewalls 33 may substantially converge at a trailing edge 34 of the ribs 30 and the ribs 30 may terminate before reaching the cylindrical wall 14 of the connector portion 6.

Figure 7:
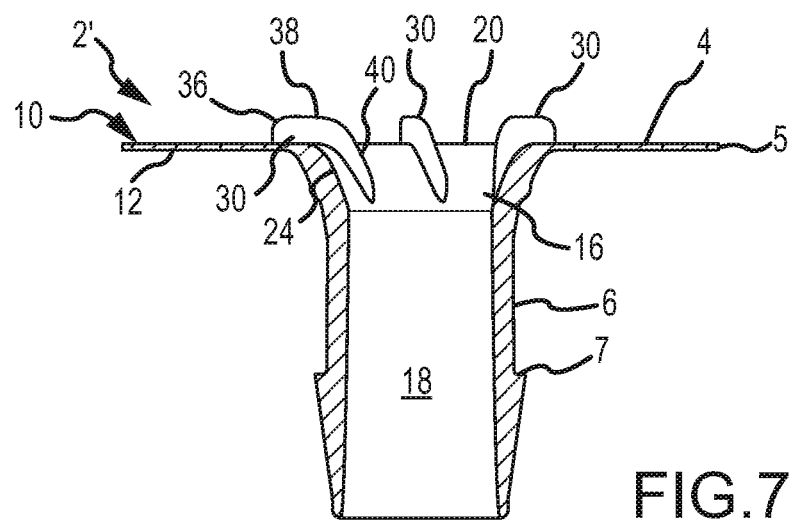
FIG. 7 is a cross-section view of the sanitary fitting of FIG. 5 taken along line 7-7 as illustrated in FIG. 6.

With reference to FIGS. 7, 8A and 8B, the suction-relief ribs 30 may be shaped along a top surface 35 of their length. Proximate the leading edge 32 of the suction-relief ribs 30, the top surface 35 may include a parabolic-shaped leading end portion 36 extending between the sidewalls 33 and angled upward with respect to the plane of the flange portion 4. (See FIG. 8B.) A middle portion 38 of the top surface 35 of the suction-relief ribs 30 may extend between the sidewalls 33 and may be flat, e.g., with a substantially constant vertical height above the flange portion 4 as the ribs extend toward the parabolic entrance 16. A proximal tapered portion 40 of the top surface 35 of the suction-relief ribs 30 may include a tapered nose geometry. The height of the proximal tapered portion 40 may taper downward as the ribs 30 extend along the parabolic entrance 16 towards the cylindrical wall 14. In one exemplary implementation, the proximal tapered portion 40 may follow a parabolic curve. For example, the shape of the proximal tapered portion 40 may follow the parabolic contour of the parabolic entrance 16 of the sanitary fitting 2 and may taper towards the surface of the parabolic entrance 16 and the cylindrical wall 14 of the connector portion 6. In other embodiments the proximal tapered portion 40 may follow another parabolic form or follow another curved form altogether.

As shown in FIGS. 7 and 8A, the tapered portion 40 of the top surface 35 may initiate tapering at the nose 20 of the flange portion 4, may taper downward along the parabolic entrance 16, and may terminate at or before reaching the cylindrical wall 14 of the connector portion 6. As explained further below, while the top surface 35 of the suction-relief ribs 30 may taper along the parabolic entrance 16, the tapered portion 40 of the top surface 35 is still a raised surface above the parabolic entrance 16. The suction-relief ribs 30 may be slightly rounded as the top edge 35 transitions to the vertically extending sidewall 33 of the vertical relief ribs 30. In addition, the vertical relief ribs 30 may flare outwardly at the intersection between the sidewalls 33 of the vertical relief ribs 30 and the flat face 10 and parabolic entrance 16, for example, to provide a contoured intersection.

The use of a parabolic entrance geometry in sanitary fittings may provide measurable benefits. For example, a streamlined, parabolic may provide a relatively lower head loss coefficient of 0.04 compared to a typical bell-mouthed fillet with a head loss coefficient of 0.10, and further when compared to a slightly rounded entrance with a head loss coefficient of 0.25.

Figure 13:
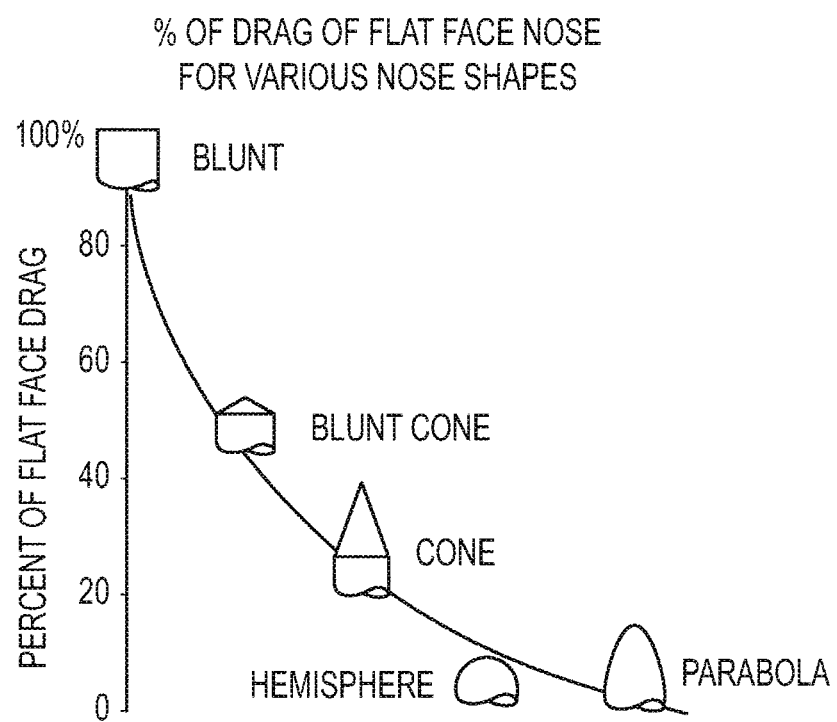
FIG. 13 is a graph illustrating a comparison of the percent of drag on a fluid for port entrances having various entrance geometries.

The benefits of providing a leading edge 32 for the suction-relief ribs 30 with a parabolic geometry versus other leading edge geometries may be appreciated in view of the graph illustrated in FIG. 13. As depicted in FIG. 13, compared with the drag for a blunt or flat face leading edges weighed at 100%, the parabolic leading edge geometry results in a lower drag force as compared to various other leading edge shapes such as blunt, blunt cone, cone, and hemisphere shapes. Accordingly, the parabolic geometry may be associated with a relatively lower drag force, which can be related to a reduction in fluid shear forces, thereby allowing a more efficient flow.

Figure 10:
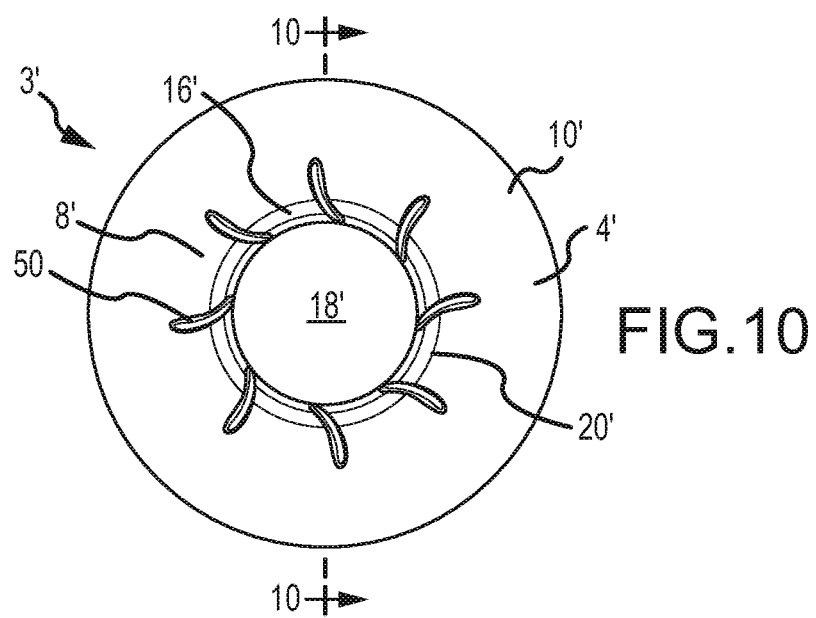
FIG. 10 is a top plan view of the sanitary fitting of FIG. 8.
Figure 11:
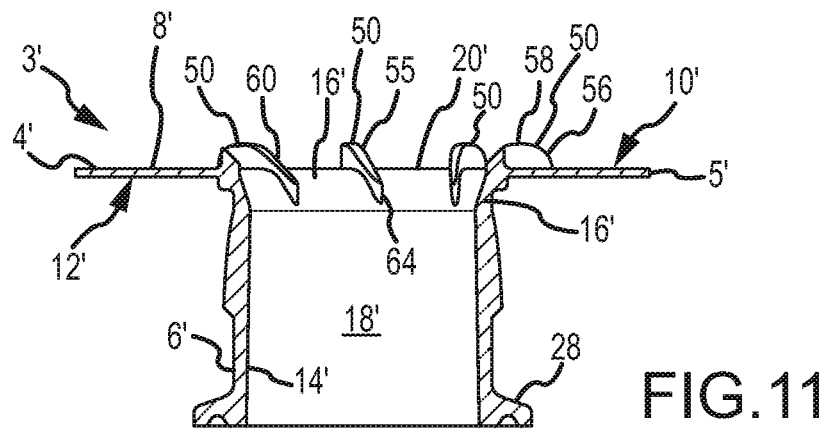
FIG. 11 is a cross-section view of the sanitary fitting of FIG. 8 taken along line 11-11 as illustrated in FIG. 10.
Figure 12:
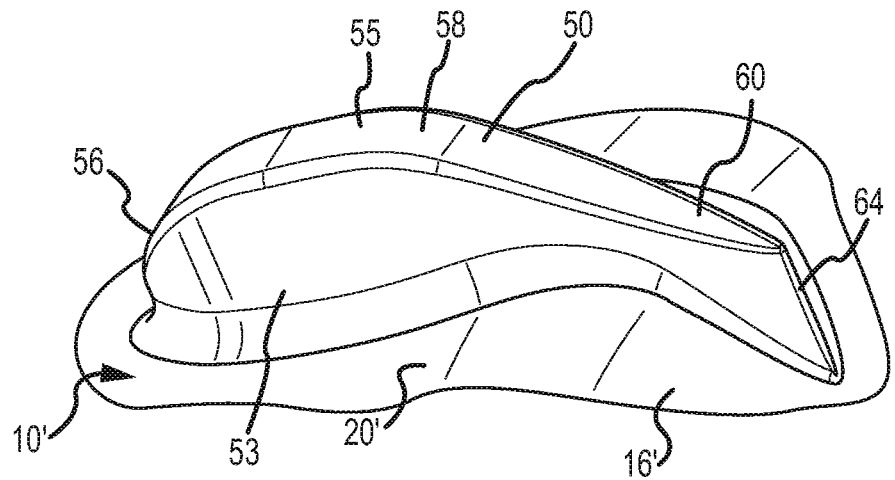
FIG. 12 is an enlarged view of a rib of the sanitary fitting of FIG. 9.

FIGS. 9-12 depict another implementation of a sanitary fitting 3' with a parabolic entrance 16' and vortex-forming suction-relief ribs 50, with features similar to FIGS. 1-3 numbered similarly. As illustrated in FIGS. 11 and 12, the ribs 50 may differ from the ribs 30 in the aspect of a more curved contour of the ribs 50 extending along a top surface 55. For example, a leading end portion 56 may curve upward from the flat surface 10; of the flange portion 4' toward a top surface 55 of the suction-relief ribs 50. As in the previous embodiment, the leading end portion 56 may also be parabolic-shaped transition laterally into the sidewalls 53 of the rib 50. A middle portion 58 of the suction-relief ribs 50 may extend along the flat face 10 of the flange portion 4 and may have a curved, rounded or parabolic-shaped vertical edge. A proximal tapered portion 60 the suction-relief ribs 50 may be shaped parabolically and may follow the contour of the parabolic entrance 16. The tapered portion 60 may initiate at the nose 20 of the flange portion 4, may taper along the parabolic entrance 16 and may terminate at or before the cylindrical wall 14 of the connector portion 6.

The top surface 55 of the ribs 50 may follow a curve from the leading end portion 56 to a trailing edge portion 64. In some implementations, this curve may follow the same parabolic form as the parabolic entrance 16, a different parabolic form, or another curve altogether, for all or a portion of the top surface. The tapering sidewalls 53 of the ribs 50 may substantially converge at a trailing edge 64 of the ribs 50 and may terminate before reaching the cylindrical wall 14 of the connector portion 6. As shown in FIG. 10, the twisting curvature, airfoil shape, and angle of pitch of the ribs 50 may be similar to that of the ribs 30.

In view of the embodiments presented in FIGS. 1-12, while the parabolic entrance of the sanitary fittings may provide for the sterile transfer of goods to and from a bag or other structure holding contents to be transferred by the sanitary fittings (e.g., sanitary fittings 2 and 3), the lead-in geometry of the parabolic entrances may promote a laminar flow of contents through the sanitary fitting. This means the parabolic entrances provided herein may offer both a reduction in flow separation and an increase in the coefficient of contraction that relates directly to the cross-sectional area of the vena contracta of the flow through an orifice. Flow separation may be understood as when fluid begins to separate itself from the boundary of the fluid. This is normally associated with vortex shedding on external flows; however, on internal flow (particularly with regard to entrance geometries) the separation aids in the formation of a vena contracta. A vena contracta may be understood as a reduction in flow cross-sectional area, which reduces the volumetric flow rate of the fluid passing through the orifice. Entrance geometry influences the formation of the vena contracta, which in turn influences flow rate of fluid passing through an orifice. With the parabolic entrances, the vena contracta and vortex shedding may be reduced, thereby increasing the efficiency of the flow rate from the flange portion and through the connector portion of the sanitary fittings.

Maintaining sterility within a sealed bag may require preventing contaminates from being introduced to the bag. As such material bags often cannot be vented, gasses may not be used to take the place of the draining media, and a vacuum may be pulled. As a result, the bag may collapse on itself as the contents drain and seal over the opening to the port in the sanitary fitting. Suction-relief may prevent the collapsing bag from blocking the flow. When the features of the vortex-forming, suction-relief ribs 30/50 (e.g., as shown in FIGS. 5-12) having a parabolic nose geometry, are combined with the geometry of the parabolic entrance 16, suction-relief may be provided by the ribs 30/50 and may prevent a bag from clogging or sealing over the central opening of the flange portion of the sanitary, which would otherwise block the flow of contents from the bag. The suction-relief ribs 30/50 provided herein may protrude normally from the flange side of the port into the bag and may extend into the opening of the port, i.e., along the parabolic entrance, to hold the bag off the opening. For example, even if a wall of the bag is sucked into the parabolic entrance, the contents of the bag may continue to flow through the channels formed between the suction-relief ribs 30/50.

Moreover, the ribs 30/50 with parabolic leading edges, parabolic and twisted sidewall shapes, rounded edges, contoured form following the parabolic entrance, and flared transitions to the flange portion and parabolic entrance avoid sharp corners and reduce the chance of the bag tearing. This may lead to reduced contamination risk from a collapsing bag tearing upon contacting standard sharp suction-relief ribs, i.e., squared-off ribs.

Fluid stagnation around suction-relief ridges can cause sediment to build up around such ridges. Fluid/particulate stagnation/sedimentation may cause blockage of the opening in a flange portion and impede flow. The parabolic leading edge of the ribs 30/50 may reduce drag and potential fluid/particulate trapping due to the reduction of flow separation and pressure drops from fluid flowing over the top surface 35/55 of the vertically extending sidewall 33/53. In addition, the parabolic-shaped leading edge of the ribs 30/50 may promote increased flow on either side of the ribs 30/50 as compared to a round radius or flat edge at the transition between the flange portion and the port portion defining the flow lumen.

Each of the ribs 30/50 may be formed with proximal tapered portions 40/60 extending along the parabolic entrances 16. The tapered portions 40/60 may be formed in a curve, which may cause flow rotation or a vortex in the contents flowing through the sanitary fitting. Inducing a vortex flow may aid in flow alignment and control of flow stability, which may contribute to optimizing the volumetric flow rate. Flow alignment may facilitate particulates flowing through the central opening 9 along the parabolic entrances 16, while flow stability may ensure laminar flow through the connector 6 to promote an increased volumetric flow rate. Causing a vortex flow by curving the proximal tapered portions 40/60 may additionally reduce the boundary layer to promote a higher volumetric flow rate. An increase in flow rate as well as the streamlined design of the ribs 30/50 may aid in the reduction of particulate build-up on or around the suction-relief ribs 30/50.

The angle of pitch of the proximal tapered portions 40/60 of the suction-relief ribs 30/50 may facilitate the formation of a vortex flow of the contents passing through the sanitary fitting. An angle of pitch between about 9 and about 12 degrees may be most advantageous, but a pitch of between about 9 and 30 degrees may facilitate vortex formation as well while reducing or preventing a turbulent flow that may create too much spin and thereby reduce the flow velocity or volume flow rate.

Figure 14:
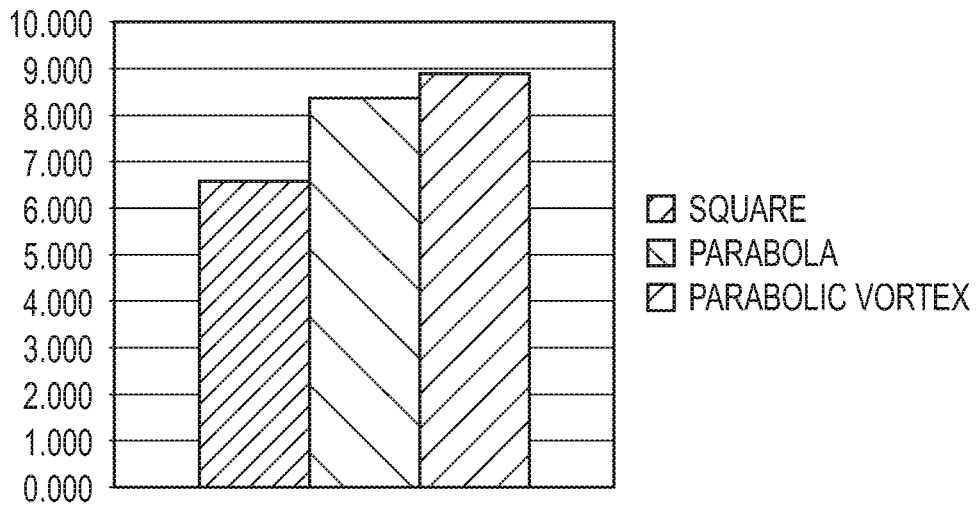
FIG. 14 is a graph illustrating a flow rate of water as a function of entrance geometry.
Figure 15:
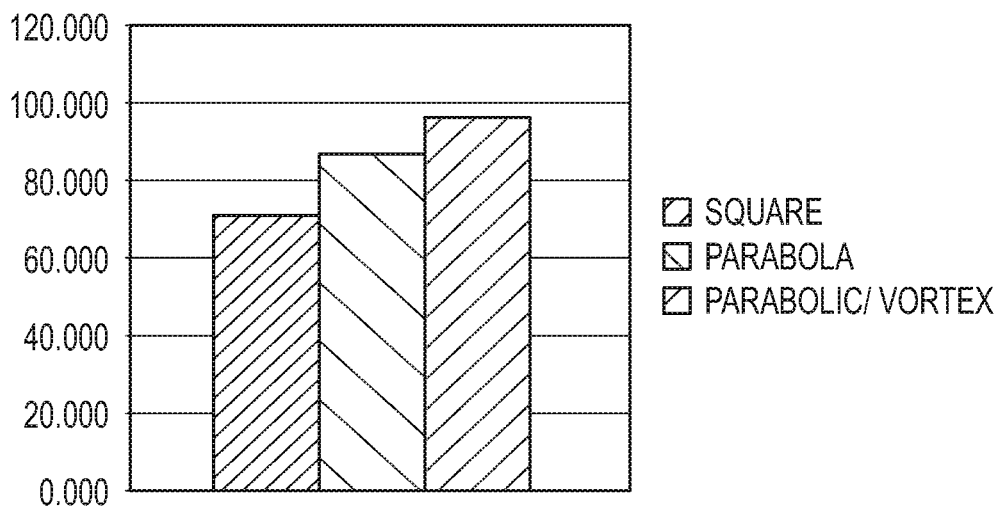
FIG. 15 is a graph illustrating a flow rate of a powder as a function of entrance geometry.

FIGS. 14 and 15 illustrate the measurable benefits that may be provided in the flow rate of fluid and powder, respectively, when using a sanitary fitting with a parabolic entrance or a sanitary fitting with both a parabolic entrance and vortex-forming suction-relief ribs as disclosed herein as compared to the use of a squared or perpendicular interface between a flange and the opening into a connector portion. In FIG. 14, the flow rate of water through a parabolic entrance to a port compared to a squared entrance to a port may be greater by approximately 20 percent, and the flow rate of water through a parabolic entrance to a port with vortex-inducing ribs compared to a squared entrance port may be greater by approximately 25 percent. The improvement in fluid flow through the ports with parabolic entrances and ports with parabolic entrances and vortex creating structures may be attributed to promotion of a laminar flow and a vortex within the flow through the lumen, whereas the square entrance may result in a turbulent flow that reduces the flow rate. In FIG. 15, the flow rate of powder through a port with a parabolic entrance compared to a squared entrance port may be greater by approximately 15 percent, and the flow rate of powder through a port with a parabolic entrance and vortex-forming suction-relief ribs compared to a squared entrance port is greater by approximately 20 percent. When compared to the results of fluid flow in FIG. 14, the rates of improvement just cited may be higher for liquid than powder. However, regardless of whether the port transports liquid or powder, both the parabolic entrance alone and the parabolic entrance with vortex-inducing suction-relief ribs may provide significant improvement in flow rate compared to the square entrance port.

All directional references (e.g., proximal, distal, upper, lower, upward, downward, left, right, lateral, front, back, top, bottom, above, below, vertical, horizontal, clockwise, and counterclockwise) are only used for identification purposes to aid the reader's understanding of the present invention, and do not create limitations, particularly as to the position, orientation, or use of the invention. Connection references (e.g., attached, coupled, connected, and joined) are to be construed broadly and may include intermediate members between a collection of elements and relative movement between elements unless otherwise indicated. As such, connection references do not necessarily infer that two elements are directly connected and in fixed relation to each other. The exemplary drawings are for purposes of illustration only and the dimensions, positions, order and relative sizes reflected in the drawings attached hereto may vary.

The above specification, examples and data provide a complete description of the structure and use of exemplary embodiments of the invention as defined in the claims. Although various embodiments of the claimed invention have been described above with a certain degree of particularity, or with reference to one or more individual embodiments, those skilled in the art could make numerous alterations to the disclosed embodiments without departing from the spirit or scope of the claimed invention. Other embodiments are therefore contemplated. It is intended that all matter contained in the above description and shown in the accompanying drawings shall be interpreted as illustrative only of particular embodiments and not limiting. Changes in detail or structure may be made without departing from the basic elements of the invention as defined in the following claims.

What is claimed is:

1. A sanitary fitting, comprising:
   a flange portion with a planar ring surface defining a central opening;
   a connector portion defining a lumen extending from the central opening toward an outlet port;
   a parabolic entrance surface extending from the planar ring surface and having a parabolic-shaped cross section with a vertex located at a transition point between the planar ring surface and the parabolic entrance surface, and further transitioning into the connector portion to define a portion of the lumen; and a plurality of suction-relief ribs positioned around the central opening and configured to cause a vortex in fluid flow through the lumen.

2. The sanitary fitting of claim 1, wherein the vertex of the parabolic entrance surface is positioned at an interface of the planar ring surface and the parabolic entrance surface.

3. The sanitary fitting of claim 1, wherein a radius of a curvature at points along the parabolic entrance surface is 0.14×D, where D is a diameter of the lumen in the connector portion below the parabolic entrance surface.

4. The sanitary fitting of claim 1, wherein the parabolic entrance surface causes an increase laminar flow of fluid passing through the sanitary fitting as compared to other curved or squared port entrance geometries with a same lumen diameter in the connector portion.

5. The sanitary fitting of claim 1, wherein the parabolic entrance surface causes an increase in flow velocity of fluid passing through the sanitary fitting as compared to other curved or squared port entrance geometries with a same lumen diameter in the connector portion.

6. The sanitary fitting of claim 1, wherein the parabolic entrance surface causes an increase in flow volume rate of fluid passing through the sanitary fitting as compared to other curved or squared port entrance geometries with a same lumen diameter in the connector portion.

7. The sanitary fitting of claim 1, wherein the suction-relief ribs are spaced equiangularly around the central opening.

8. The sanitary fitting of claim 1, wherein the suction-relief ribs extend partially on the planar ring surface and partially along the parabolic entrance surface.

9. The sanitary fitting of claim 1, wherein the suction-relief ribs are formed with a twisting curvature extending along the parabolic entrance.

10. The sanitary fitting of claim 1, wherein a leading end of the suction-relief ribs is parabolic in shape.

11. The sanitary fitting of claim 1, wherein a top surface of the suction-relief ribs tapers towards the lumen in the connector portion.

12. The sanitary fitting of claim 1, wherein sidewalls of the suction-relief ribs comprise an airfoil shape.

13. The sanitary fitting of claim 1, wherein the lumen extending through the connector portion below the parabolic entrance surface is formed by a cylindrical wall of the connector portion.

14. The sanitary fitting of claim 1, wherein an outer diameter of the parabolic entrance surface is greater than a diameter of the lumen extending through the connector portion below the parabolic entrance surface.

15. A sanitary fitting, comprising:
a flange portion defining a flat face and a central opening therein;
a connector portion extending from the flange portion and defining an outlet port;
a parabolic entrance to the outlet port formed by a continuous sidewall that defines the central opening extending from an inner perimeter edge of the flat face to the outlet port of the connector portion; and
a suction-relief rib arranged along the flat face of the flange portion and extending into the parabolic entrance, wherein the suction-relief rib comprises a twisting curvature for causing rotation of fluid flow through the sanitary fitting.

16. The sanitary fitting of claim 15, wherein the suction-relief rib comprises a parabolic-shaped leading end.

17. The sanitary fitting of claim 15, wherein the suction-relief rib comprises a generally flat top surface that tapers downward to gradually decrease a height of the suction-relief rib as the suction-relief rib extends along the parabolic entrance toward the outlet port.

18. The sanitary fitting of claim 15, wherein:
the suction-relief rib comprises sidewalls forming an airfoil shape extending generally normal to the flat face and parabolic entrance,
the airfoil shape comprises a parabolic-shaped leading edge that transitions into the sidewalls;
a thickness between the sidewalls remains substantially constant as the suction-relief rib extends along the flat face towards the parabolic entrance, and
the thickness between the sidewalls narrows as the suction-relief rib extends into the parabolic entrance and tapers to terminate at a trailing end.

19. The sanitary fitting of claim 18, wherein the sidewall comprises the twisting curvature as the suction-relief rib extends into the parabolic entrance.

20. The sanitary fitting of claim 18, wherein the suction-relief rib comprises a parabolically shaped top edge and sidewall.

21. A sanitary fitting comprising:
a flange portion having a planar ring surface;
a connector portion extending from the flange portion and defining a lumen therethrough having an axis normal to the planar ring surface; and
a plurality of suction-relief ribs positioned at least partially on and protruding from the planar ring surface of the flange portion around an entrance opening to the lumen and configured to cause a vortex in fluid flow through the lumen.

22. The sanitary fitting of claim 21, wherein sidewalls of the plurality of suction-relief ribs comprise an airfoil shape having a leading edge that is wider than a trailing edge.

23. The sanitary fitting of claim 22, wherein the plurality of suction-relief ribs form a curved shape from the leading edge to the trailing edge.

* * * * *